US011458178B2

(12) United States Patent
Yamato et al.

(10) Patent No.: US 11,458,178 B2
(45) Date of Patent: Oct. 4, 2022

(54) METHOD FOR ALLEVIATING FATIGUE

(71) Applicants: RIKEN, Saitama (JP); OZEKI CORPORATION, Hyogo (JP)

(72) Inventors: Masanori Yamato, Saitama (JP); Yosky Kataoka, Saitama (JP); Yasuhisa Tamura, Saitama (JP); Satoshi Kume, Saitama (JP); Toshitaka Minetoki, Hyogo (JP); Kazuhisa Hizume, Hyogo (JP); Satoshi Okazaki, Hyogo (JP); Miyo Hirata, Hyogo (JP); Shinya Okuda, Hyogo (JP); Takayuki Bogaki, Hyogo (JP)

(73) Assignees: RIKEN, Saitama (JP); OZEKI CORPORATION, Hyogo (JP)

( * ) Notice: Subject to any disclaimer, the term of this patent is extended or adjusted under 35 U.S.C. 154(b) by 109 days.

(21) Appl. No.: 16/765,070

(22) PCT Filed: Nov. 26, 2018

(86) PCT No.: PCT/JP2018/043374
§ 371 (c)(1),
(2) Date: Sep. 25, 2020

(87) PCT Pub. No.: WO2019/103138
PCT Pub. Date: May 31, 2019

(65) Prior Publication Data
US 2021/0106634 A1    Apr. 15, 2021

(30) Foreign Application Priority Data

Nov. 24, 2017  (JP) .............................. JP2017-226305

(51) Int. Cl.
*A61K 36/06*  (2006.01)
*A23L 33/10*  (2016.01)
*A61P 25/00*  (2006.01)
*A23L 2/52*  (2006.01)

(52) U.S. Cl.
CPC ................ *A61K 36/06* (2013.01); *A23L 2/52* (2013.01); *A23L 33/10* (2016.08); *A61P 25/00* (2018.01)

(58) Field of Classification Search
None
See application file for complete search history.

(56) References Cited

U.S. PATENT DOCUMENTS

| 2015/0273058 | A1 |   | 10/2015 | Smith et al. |
|---|---|---|---|---|
| 2018/0214505 | A1 |   | 8/2018  | Ano et al. |
| 2021/0301232 | A1 | * | 9/2021  | Clancy .................. C12G 1/005 |

FOREIGN PATENT DOCUMENTS

| JP | 2009/221135  | * | 10/2009 |
|----|--------------|---|---------|
| JP | 2009-221135  |   | 10/2009 |
| JP | 2009/292785  | * | 12/2009 |
| JP | 2009-292785  |   | 12/2009 |
| JP | 2013/177330  | * | 9/2013  |
| JP | 2013-177330  |   | 9/2013  |
| JP | 2015-157855  |   | 9/2015  |
| JP | 2016-222646  |   | 12/2016 |
| WO | 2004/062675  |   | 7/2004  |

OTHER PUBLICATIONS

Yamato, Masanori et al., "Anti-inflammatory . . . ", Nippon Hiro Gakkaishi, May 27, 2017, vol. 13, No. 1, p. 75.
Katafuchi, Toshihiko et al., "Fatigue conditioning and serotonin", Separate volume: Igaku no ayumi, Science of fatigue, Feb. 1, 2003, vol. 204, No. 5, pp. 46-50.
Kataoka, Yosuke, Japanese Journal of Biological Psychiatry, 2013, vol. 24, No. 4, pp. 211-217.
Yamato, Masanori et al., "Brain Interleukin-1 β and the Intrinsic Receptor Antagonist Control Peripheral Toll-Like Receptor 3-Mediated Suppression of Spontaneous Activity in Rats", PLOS ONE, Mar. 2014, vol. 9, Issue. 3, e90950, pp. 1-9, especially Abstract.
English Translation of International Preliminary Report on Patentability of PCT/JP2018/043374, dated May 26, 2020, 11 pages.
International Search Report for PCT/JP2018/043374, dated Feb. 19, 2019, 2 pages.

* cited by examiner

*Primary Examiner* — Ralph J Gitomer
(74) *Attorney, Agent, or Firm* — Casimir Jones, SC; Robert A. Goetz

(57) ABSTRACT

The present invention provides a novel IL-1β and/or IL-6 expression inhibitor and use thereof. The IL-1β and/or IL-6 expression inhibitor in accordance with an aspect of the present invention contains a component derived from alcoholic fermentation lees.

12 Claims, 2 Drawing Sheets

FIG. 1

EXPERIMENT SCHEDULE

| | Day -7 | | 0 Vehicle or Poly I:C administration | Sampling |
|---|---|---|---|---|
| | | Prior ingestion for 7 days | ↓ ←5 hours→ | ↓ |
| (1) Vehicle + regular diet group | | Regular diet | Obtain brain samples (cerebral cortex, hippocampus) ↓ qRT-PCR (IL-1β, IL-6, TNF-α) | |
| (2) Poly I:C + regular diet group | | Regular diet | | |
| (3) Poly I:C + SLE diet group | | SLE diet | [REMARKS] Regular diet: MF (Oriental Yeast) Poly I:C (GE Healthcare) was intraabdominally administered by 10 mg/kg Vehicle: Physiological saline solution Fasting started 2 hours before sampling | |
| (4) Poly I:C + RFSLE diet group | | RFSLE diet | | |
| (5) Poly I:C + lactic fermented RFSLE diet group | | Lactic refermented RFSLE diet | | |

METHOD FOR ALLEVIATING FATIGUE

TECHNICAL FIELD

The present invention relates to an IL-1β and/or IL-6 expression inhibitor which inhibits expression of IL-1β and/or IL-6 and contains a component derived from alcoholic fermentation lees, and to use of the IL-1β and/or IL-6 expression inhibitor.

BACKGROUND ART

In modern societies, a feeling of lassitude is one of main reasons why a patient visits a medical institution. A feeling of lassitude is caused by a variety of factors, such as overwork, psychological stress, and disease, and is considered to be one of key signals that indicate constant disorders in a patient.

In recent years, it has been elucidated that fatigue is recognized in the brain and thus develops as a feeling of lassitude, and that the brain is also deeply involved in lowering of working efficiency by fatigue. For example, the inventors of the present invention have shown that production of an inflammatory substance, such as interleukin-1β (IL-1β), in the brain triggers the development of at least some sort of feeling of lassitude (Non-Patent Literature 1).

Methods for alleviating a feeling of lassitude are being actively developed. For example, Patent Literature 1 describes a composition containing an oligopeptide having a specific amino acid sequence for mitigating a symptom such as chronic fatigue syndrome. Moreover, Patent Literature 2 discloses a fatigue relief agent containing a peptide mixture that is obtained by treatment of sake lees with a proteolytic enzyme derived from *Bacillus stearothermophilus*.

CITATION LIST

Patent Literature

[Patent Literature 1]
Japanese Patent Application Publication Tokukai No. 2016-222646 (Publication date: Dec. 26, 2016)
[Patent Literature 2]
Japanese Patent Application Publication, Tokukai, No. 2009-221135 (Japanese Patent No. 5317501) (Publication Date: Oct. 1, 2009)

Non-Patent Literature

[Non-Patent Literature 1]
PLOS ONE, 2014 (Published: Mar. 12, 2014, https://doi.org/10.1371/journal.pone.0090950): Brain Interleukin-1β and the Intrinsic Receptor Antagonist Control Peripheral Toll-Like Receptor 3-Mediated Suppression of Spontaneous Activity in Rats; Masanori Yamato, Yasuhisa Tamura, Asami Eguchi, Satoshi Kume, Yukiharu Miyashige, Masayuki Nakano, Yasuyoshi Watanabe, Yosky Kataoka

SUMMARY OF INVENTION

Technical Problem

However, few of the methods for alleviating a feeling of lassitude developed so far have been well substantiated by use of human or animal individuals in terms of their alleviation effects.

For example, in Patent Literature 1, an effect of a composition on microglia which is an immunocyte is observed while using, as an indicator, production of an inflammatory cytokine in the isolated microglia. However, effects on humans or non-human animals have only been assessed based on exploratory behaviors of mice.

In Patent Literature 2, although a fatigue relief agent is administered to a human and an effect thereof is assessed, the assessment method is merely qualitative.

An object of the present invention is to provide a novel IL-1p and/or IL-6 expression inhibitor and use thereof based on a molecular mechanism of onset of a feeling of lassitude.

Solution to Problem

In order to attain the object, the inventors diligently studied and have consequently arrived at the following invention.
(1) An IL-1β and/or IL-6 expression inhibitor which inhibits expression of IL-1β and/or IL-6, the IL-1β and/or IL-6 expression inhibitor containing a component derived from alcoholic fermentation lees.

Advantageous Effects of Invention

According to an aspect of the present invention, the novel IL-1β and/or IL-6 expression inhibitor can be obtained and, for example, the IL-1β and/or IL-6 expression inhibitor can be used to obtain an anti-fatigue effect.

BRIEF DESCRIPTION OF DRAWINGS

FIG. 1 shows an experiment schedule to verify effects of sake-lees extracts in Examples of the present invention.

DESCRIPTION OF EMBODIMENTS

Figure 2:
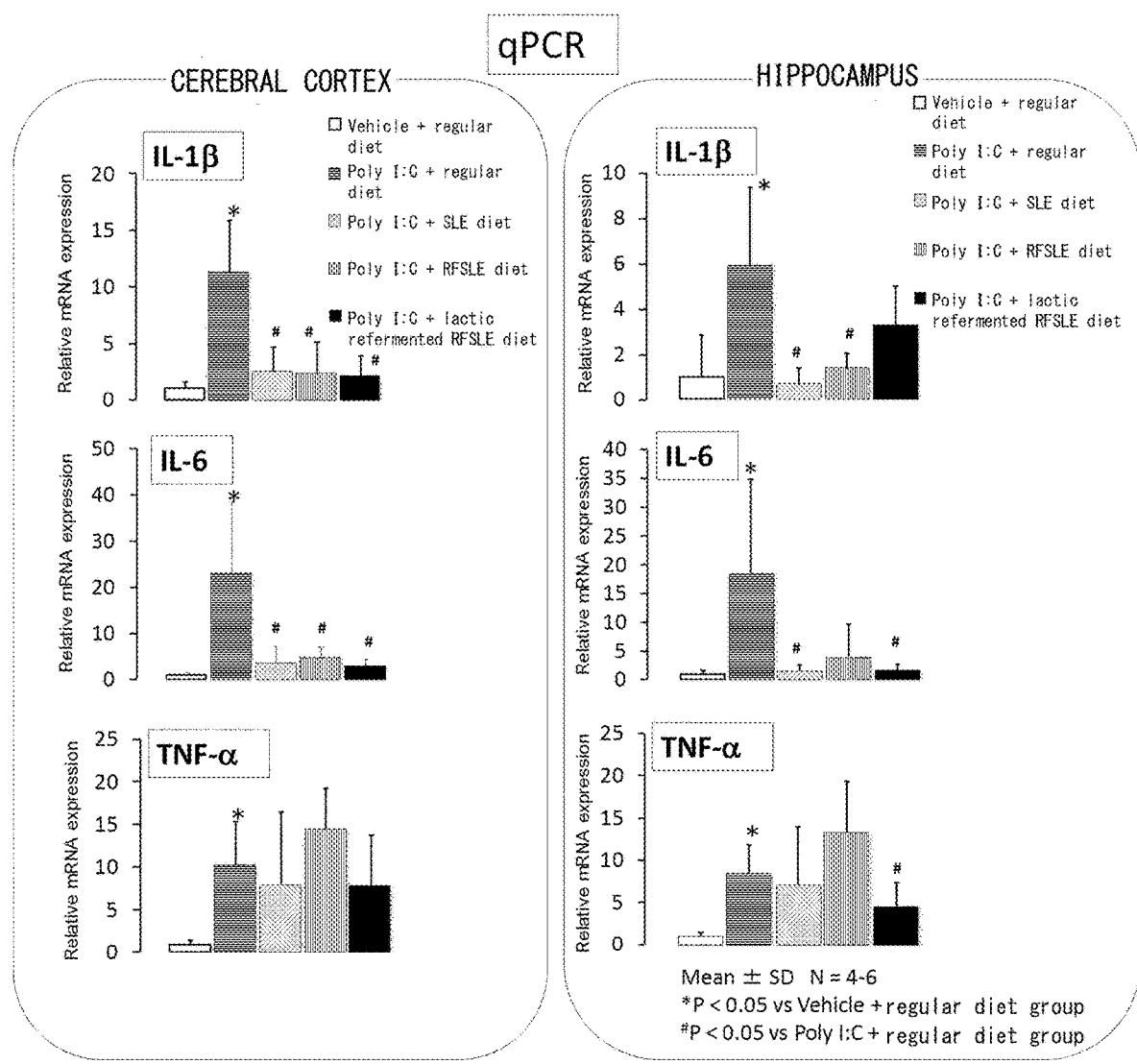
FIG. 2 is a graph showing an amount of mRNA expression of various inflammatory cytokines in a cerebral cortex and a hippocampus observed with a qPCR method in Examples of the present invention.

The following description will discuss embodiments of the present invention in detail. Note, however, that the present invention is not limited to those embodiments, and can be made in an aspect obtained by variously altering the embodiments within the described scope. Note that numerical expressions such as "A to B" herein mean "not less than A and not more than B" unless otherwise stated.

The following description will discuss an embodiment of the present invention. The present invention is, however, not limited to the embodiment below.

[1. IL-1β and/or IL-6 Expression Inhibitor]

The expression inhibitor in accordance with an aspect of the present invention contains a component derived from alcoholic fermentation lees and inhibits expression of IL-1β and/or IL-6 which are representative inflammatory cytokines. In this specification, "A and/or B" includes both "A and B" and "A or B".

<Inflammatory Cytokine and Inhibition of Expression Thereof>

An inflammatory cytokine is a small protein secreted by a cell, and the inflammatory cytokine increases inflammation and exacerbates a disease. In a case where IL-1β or IL-6 is administered to a human, the IL-1β or IL-6 causes fever, inflammation, or disruption of cells and tissues throughout the body, and may result in death from shock. Secretion of the inflammatory cytokine is triggered by stress such as injury, infection, anoxia, or exposure to a toxic substance. The stress is not limited to that caused physically, and includes stress caused psychologically. The expression inhibitor in accordance with an aspect of the present invention inhibits expression of at least one of IL-1β and IL-6, preferably both IL-1β and IL-6, under stress where inflammatory cytokines can be produced. That is, the expression inhibitor in accordance with an aspect of the present invention is an expression inhibitor of IL-1β, an expression inhibitor of IL-6, or an expression inhibitor of IL-1β and IL-6. Note that the expression inhibitor in accordance with an aspect of the present invention may not be significantly effective in inhibiting expression of TNF-α which is a type of inflammatory cytokines, or may exhibit a lower expression inhibitory effect on TNF-α as compared with an expression inhibitory effect on IL-1β and/or IL-6.

Here, cases where the expression of an inflammatory cytokine is inhibited can be cases where 1) transcription to mRNA encoding an inflammatory cytokine is inhibited, and 2) translation from the mRNA into a protein is inhibited, as compared with a case where the expression inhibitor is not used. It may be preferable to exhibit an inhibiting effect of at least 1).

<Alcoholic Fermentation Lees>

The expression inhibitor in accordance with an aspect of the present invention contains a component derived from alcoholic fermentation lees. The term "alcoholic fermentation lees" is a generic term for a residue, that is, liquor pomace which is generated in an alcoholic fermentation process in which a raw material containing a saccharide (e.g., glucose, fructose, sucrose, or the like) is subjected to alcoholic fermentation to obtain alcohol (ethyl alcohol).

The raw material containing the saccharide can be, for example, a saccharified product obtained from a starchy material such as rice (including whole rice), barley (including malt), tuber or root, corn, bean, or buckwheat. Alternatively, a material such as fruit juice of grape, which is originally rich in saccharides, can be used as the raw material containing the saccharide as it is. The material used here is preferably rice and barley, more preferably rice.

Examples of liquor pomace include whisky lees, fruit wine lees (such as pomace of grape wine), sake lees (pomace of sake), shochu lees, and the like, and sake lees and shochu lees are preferable, and sake lees are more preferable.

Sake lees include, for example, normal-quality sake lees, high-quality sake lees, and liquefied sake lees. Sake lees may be or may not be heat-sterilized. Seed malt used in saccharifying rice starch in the process of making sake includes black koji, white koji, and yellow koji, and yellow koji is sometimes preferable. Meanwhile, seed malt used in the process of making shochu includes black koji, white koji, and yellow koji, and black koji or white koji is sometimes preferable.

<Examples of Component Derived from Alcoholic Fermentation Lees Contained in Expression Inhibitor and Preparation Thereof>

Examples of a component which is derived from alcoholic fermentation lees and is contained in the expression inhibitor in accordance with an aspect of the present invention include, in addition to alcoholic fermentation lees per se, the following preparation products and the like obtained with use of alcoholic fermentation lees. Note, however, that the component is not limited to those examples.

(1) Water extract of alcoholic fermentation lees, etc.

In an aspect of the present invention, a component derived from alcoholic fermentation lees can be a water extract of alcoholic fermentation lees or a solid content obtained after water extraction. Alcoholic fermentation lees are made into a suspension by addition of water in the water extraction. A temperature of water extraction is not particularly limited. For example, extraction is carried out with water at 20° C. to 100° C. or higher, and extraction is preferably carried out with water at 60° C. to 80° C. or higher. A time of extraction is not particularly limited. For example, the time is within a range from 30 minutes to 6 hours, and preferably within a range from 1 hour to 3 hours. After the extraction operation, the obtained extract can be optionally divided into an extraction liquid (alcoholic fermentation lees extract) and a solid content by solid-liquid separation. As a method of solid-liquid separation, for example, a method described in (2) below can be used.

The extraction liquid thus obtained can be concentrated by optionally removing water to obtain a concentrated liquid of the alcoholic fermentation lees extract. The concentrated liquid thus obtained may be optionally dried to a powder state. A specific drying method is not particularly limited, and examples of the drying method include freeze drying, drum drying, spray drying, and the like.

(2) Refermented Product Obtained by Alcoholic Fermentation of Alcoholic Fermentation Lees In an aspect of the present invention, a component derived from alcoholic fermentation lees can be a refermented product obtained by alcoholic fermentation of the above-described alcoholic fermentation lees (preferably sake lees). Here, the refermented product encompasses: a liquid portion only of the refermented product; a solid content only of the refermented product; a processed product of those (such as a powdery product obtained from the liquid portion); and the like.

The alcoholic fermentation lees are optionally subjected to amylolytic enzyme treatment and/or proteolytic enzyme treatment (hereinafter sometimes collectively referred to as "enzyme treatment") and to fermentation treatment with yeast (alcoholic fermentation treatment).

Alcoholic fermentation lees are made into a suspension by addition of water in the enzyme treatment and in the fermentation treatment. At this time, the following enzyme, yeast, organic acid, and/or the like can be added simultaneously, or those can be added to alcoholic fermentation lees in a form of suspension or of aqueous solution.

In an aspect of the present invention, alcoholic fermentation lees are pH-adjusted prior to the enzyme treatment and/or the fermentation treatment. Preferably, the pH adjustment is carried out using an acid. The acid used in this case can be any one as long as the acid can be used in food and, for example, it is possible to use inorganic acids such as phosphoric acid and hydrochloric acid, organic acids such as acetic acid, citric acid, lactic acid and succinic acid, and the like. Preferably, the acid is an organic acid, and further preferably lactic acid.

When the pH adjustment is carried out, it is preferable to adjust the pH to not higher than pH5, preferably lower than pH5, more preferably not higher than pH4.5. Exemplary preferable pHs are pH2 to pH5, pH2.5 to pH5, pH2.5 to pH4.5, pH3 to pH4.8, pH3.5 to pH4.5, and the like.

In an aspect of the present invention, the optional amylolytic enzyme treatment, the optional proteolytic enzyme treatment, and the fermentation treatment with yeast can be carried out in any order, and it is possible to simultaneously carry out two of those treatments, and carry out the rest one treatment before or after those two treatments. Alternatively, all of those treatments can be carried out simultaneously. By carrying out all the treatments simultaneously, it is possible to shorten the production time of the composition derived from alcoholic fermentation lees and to simplify processes and equipment.

In an aspect of the present invention, an amylolytic enzyme to be used can be any one usable in food. For example, it is possible to use an amylolytic enzyme derived from filamentous fungi such as koji mold, an amylolytic enzyme derived from bacteria such as *Bacillus subtilis*, or the like. Examples of the amylolytic enzyme include amylases such as α-amylase and glucoamylase, glucosidases such as α-glucosidase and transglucosidase, and debranching enzymes such as pullulanase and isoamylase. Those enzymes can be purified products or crude products. It is possible to use a substance such as pancreatin which contains another enzyme such as a proteolytic enzyme in addition to an amylolytic enzyme. Alternatively, it is possible to use a commercially available amylolytic enzyme agent. The commercially available amylolytic enzyme agent can be Gluc 100 (available from Amano Enzyme Inc.), Gluc SB (available from Amano Enzyme Inc.), Gluczyme AF6 (available from Amano Enzyme Inc.), Kokugen L (available from Daiwa Fine Chemicals Co., Ltd.), Spitase CP-40FG (available from Nagase ChemteX Corporation), Sumizyme S (available from SHINNIHON CHEMICALS Corporation), Biozyme A (available from Amano Enzyme Inc.), Kleistase L1 (available from Daiwa Fine Chemicals Co., Ltd.), Kokulase-G2 (available from Sankyo Lifetech Co., Ltd.), or the like. The amylolytic enzyme or the enzymatic agent can be one type or can be two or more types. The amylolytic enzymes and commercially available amylolytic enzyme agents are merely examples, and enzymes other than those described above can be appropriately selected and used depending on a type of raw material, a treatment amount, a target product, and the like.

In an aspect of the present invention, a proteolytic enzyme to be used can be any one usable in food. For example, it is possible to use a proteolytic enzyme derived from filamentous fungi such as koji mold, a proteolytic enzyme derived from bacteria such as *Bacillus subtilis*, papain derived from a plant, pepsin or trypsin derived from an animal, or the like. Examples of the proteolytic enzyme include peptidases and the like. Those enzymes can be purified products or crude products. It is possible to use a substance such as pancreatin which contains another enzyme such as an amylolytic enzyme in addition to a proteolytic enzyme. Alternatively, it is possible to use a commercially available proteolytic enzyme agent. The commercially available proteolytic enzyme agent can be Pepsin (available from Wako Pure Chemical Industries, Ltd.), Orientase 20A (available from Hbi Enzymes Inc.), Orientase 90N (available from Hbi Enzymes Inc.), Orientase ONS (available from Hbi Enzymes Inc.), Newlase F3G (available from Amano Enzyme Inc.), Protease A "Amano" G (available from Amano Enzyme Inc.), Protease M "Amano" G (available from Amano Enzyme Inc.), Sumizyme AP (available from SHINNIHON CHEMICALS Corporation), Sumizyme LP (available from SHINNIHON CHEMICALS Corporation), or the like. The proteolytic enzyme or the enzymatic agent can be one type or can be two or more types. The proteolytic enzymes and commercially available proteolytic enzyme agents are merely examples, and proteolytic enzymes other than those described above can be appropriately selected and used depending on a type of raw material, a treatment amount, a target product, and the like.

Preferably, the alcoholic fermentation treatment with yeast is carried out before or after the amylolytic enzyme treatment and/or the proteolytic enzyme treatment, or in parallel with the treatment(s). In an aspect of the present invention, yeast to be used can be any one usable in food. For example, it is possible to use yeast such as sake yeast, beer yeast, wine yeast, or baker's yeast or, as another classification, yeast of, for example, the genus *Saccharomyces*, the genus *Zygosaccharomyces*, the genus *Schizosaccharomyces*, or the genus *Pichia*. In an aspect of the present invention, yeast used to produce a refermented product of alcoholic fermentation lees can be one type or can be two or more types. Those types of yeast are merely examples, and yeast other than those described above can be appropriately selected and used depending on a type of raw material, a treatment amount, a target product, and the like.

After the enzyme treatment and the alcoholic fermentation treatment with yeast which are optionally carried out, a reactant is preferably heated to inactivate the enzyme and yeast. A heating condition for inactivation can be appropriately adjusted by a person skilled in the art, and an example can be heating until reaching a temperature of 70° C. Alternatively, activities of the enzyme and yeast can be maintained by not heating the reactant.

The obtained reactant (i.e., the refermented product) is subjected to solid-liquid separation to extract the liquid portion as an alcohol-lees fermented extract (i.e., a part (liquid portion) of the above refermented product). The solid-liquid separation method used can be a method known to those skilled in the art and, for example, centrifugation, filtration, decantation, or the like can be used. Depending on factors such as an amount of necessary material and a nature of precipitate, the above solid-liquid separation method or another solid-liquid separation method can be appropriately selected or those methods can be used in combination.

From the alcohol-lees fermented extract, alcohol can be removed as needed. The alcohol-lees fermented extract can be concentrated by optionally removing water to obtain a concentrated liquid of the alcohol-lees fermented extract. The concentrated liquid thus obtained can be optionally dried to a powder state. A specific drying method is not particularly limited, and examples of the drying method include freeze drying, drum drying, spray drying, and the like.

(3) Refermented Product Obtained by Lactic Acid Fermentation of Alcohol-Lees Fermented Extract In an aspect of the present invention, the component derived from alcoholic fermentation lees can be a refermented product obtained by lactic acid fermentation of the alcoholic fermentation lees extract (which can be a concentrated liquid thereof) obtained in (2) above. Here, the refermented product encompasses: a liquid portion only of the refermented product; a processed product thereof (such as a powdery product obtained from the liquid portion); and the like.

In one preferable aspect of the present invention, the component derived from alcoholic fermentation lees is a refermented product obtained by (i) subjecting, to lactic acid fermentation, the sake-lees fermented extract (alcohol-lees fermented extract) obtained by subjecting sake lees to the amylolytic enzyme treatment and/or the proteolytic enzyme treatment, and the alcoholic fermentation treatment with yeast, and then (ii) carrying out solid-liquid separation to remove a solid content.

To the alcoholic fermentation lees extract (which can be a concentrated liquid thereof) obtained in (2) above, it is possible to add a component such as sugar which assists fermentation if needed.

Lactic acid bacteria used in lactic acid fermentation include a microorganism of the genus *Lactobacillus*. The microorganism of the genus *Lactobacillus* used is preferably

*Lactobacillus brevis* or *Lactobacillus hilgardii*. Those can be used alone or two or more types of those can be used in combination. Examples of a preferable *Lactobacillus* microorganism include *Lactobacillus hilgardii* strain 376-80 (accession number; P-02160), *Lactobacillus hilgardii* strain 301-259 (accession number; P-02161), *Lactobacillus brevis* strain 301-282 (accession number; P-02167), and the like.

Conditions for fermentation by the microorganism of the genus *Lactobacillus* can be appropriately adjusted by those skilled in the art. As specific fermentation conditions, for example, a preferable temperature condition can be 20 to 40° C., 20 to 37° C., 25 to 40° C., 25 to 37° C., 25 to 30° C., or 30 to 40° C., and a preferable period of time can be 20 hours or more, 20 hours to 5 days, 20 hours to 50 days, 1 day or more, 1 to 7 days, 1 to 14 days, 1 to 50 days, 2 to 14 days, 2 to 21 days, 5 to 15 days, 5 to 21 days, or 5 to 50 days.

The fermentation by the microorganism of the genus *Lactobacillus* yields a lactic-acid fermented extract of the alcoholic fermentation lees (i.e., a refermented product obtained by lactic acid fermentation).

The obtained lactic-acid fermented extract can be used as it is, or a liquid portion (i.e., the lactic-acid fermented extract (liquid portion)) obtained by removing bacterial cells from the lactic-acid fermented extract can be used. The method of removing bacterial cells used can be a method known to those skilled in the art and, for example, centrifugation, filtration, or the like can be used. The obtained lactic-acid fermented extract can be concentrated and adjusted to have an appropriate concentration, if desired. A method known to those skilled in the art can be used as a means of concentration. For example, the concentration can be carried out by an evaporator or the like.

The concentrated liquid thus obtained can be dried to a powder state. A specific drying method is not particularly limited, and examples of the drying method include freeze drying, drum drying, spray drying, and the like.

(4) Refermented Product Obtained by Lactic Acid Fermentation of Alcoholic Fermentation Lees In an aspect of the present invention, a component derived from alcoholic fermentation lees can be a refermented product obtained by lactic acid fermentation of the above-described alcoholic fermentation lees (preferably sake lees). Here, the refermented product encompasses: a liquid portion only of the refermented product; a solid content only of the refermented product; a processed product of those (such as a powdery product obtained from the liquid portion); and the like.

The alcoholic fermentation lees are optionally subjected to the amylolytic enzyme treatment and/or the proteolytic enzyme treatment and to the fermentation treatment with lactic acid bacteria (lactic acid fermentation treatment). Those enzyme treatments can be carried out in a manner similar to the enzyme treatments described above in "(2) Refermented product obtained by alcoholic fermentation of alcoholic fermentation lees". In addition, the lactic acid fermentation treatment can be carried out in a manner similar to the lactic acid fermentation treatment described above in "(3) Refermented product obtained by lactic acid fermentation of alcohol-lees fermented extract".

The obtained reactant (i.e., the refermented product) is subjected to solid-liquid separation to extract the liquid portion as a lactic-acid fermented extract (i.e., a part (liquid portion) of the above refermented product). The obtained lactic-acid fermented extract can be used as it is, or a liquid portion (i.e., the lactic-acid fermented extract (liquid portion)) obtained by removing bacterial cells from the lactic-acid fermented extract can be used. The obtained lactic-acid fermented extract can be concentrated and adjusted to have an appropriate concentration, if desired.

The concentrated liquid thus obtained can be dried to a powder state. A specific drying method is not particularly limited, and examples of the drying method include freeze drying, drum drying, spray drying, and the like.

Note that the above (2) to (4) are examples corresponding to the refermented product obtained by carrying out lactic acid fermentation and/or alcoholic fermentation of alcoholic fermentation lees at least once. It is also possible to obtain another form of refermented product by carrying out lactic acid fermentation and/or alcoholic fermentation of alcoholic fermentation lees at least once through a modified process which can be, for example, a process including a plurality of lactic acid fermentation steps, a process including a plurality of alcoholic fermentation steps, a process in which the order of the steps is changed, or the like.

<Form of Expression Inhibitor>

In an aspect of the present invention, the expression inhibitor contains the component derived from alcoholic fermentation lees as described above. The expression inhibitor can be a component derived from alcoholic fermentation lees as it is, or can be an agent in which other raw materials generally used in each product are added to the component.

[2. Applications of Expression Inhibitor]

The expression inhibitor in accordance with an aspect of the present invention can be used as an IL-1β and/or IL-6 expression inhibitor itself (e.g., used as a reagent or the like) and can be used, for example, in products such as food or beverage compositions, food or beverage additives, seasonings, medicines, and cosmetics.

Examples of the food or beverage composition include a supplement, a food or beverage for one or more specified health uses, and a food or beverage with one or more functional claims, and a food or beverage with one or more nutrient function claims.

Those products containing an effective amount of the expression inhibitor exhibit an expression inhibitory property with respect to IL-1β and/or IL-6. Therefore, functions and efficacy, such as an anti-inflammatory effect and/or an anti-fatigue effect, can be indicated. For example, in cases of a food or beverage for one or more specified health uses, a food or beverage with one or more functional claims, a food or beverage with one or more nutrient function claims, and the like, the functional claims are of an anti-inflammatory effect, an anti-fatigue effect, and/or the like and, in a case of a medicine, the functional claim is of an anti-inflammatory medicine, an anti-fatigue medicine, or the like.

It should be noted that anti-inflammation refers to prevention of inflammation and/or alleviation of inflammation, and a preferable aspect can be prevention of inflammation (to confer, on an individual, resistance to a predisposition to inflammation). Inflammation refers to inflammation that occurs in the body and inflammation that occurs externally, and is preferably inflammation that occurs in the body, more preferably inflammation in the brain. Inflammation in the brain is particularly considered as a predisposition to psychological fatigue.

Anti-fatigue refers to prevention of fatigue and/or alleviation of fatigue, and a preferable aspect can be prevention of fatigue (to confer, on an individual, resistance to a predisposition to fatigue). Fatigue refers to both physical fatigue and psychological fatigue, preferably psychological fatigue, among which chronic fatigue syndrome can be a preferable subject. Chronic fatigue syndrome is a long-lasting illness of at least 6 months duration during which symptoms such as severe systemic malaise, low-grade fever, lymphadenopathy, headache, muscle weakness, sleep disorder, and poor thinking/concentration which are severe enough to notably impair life do not resolve even after rest. In severe cases, care may be needed throughout life.

In an aspect of the present invention, the expression inhibitor can be formulated in each product with a known method. A blending amount of the expression inhibitor, other blending components, and the like are not particularly limited. Examples of other raw materials include a seasoning, an acidulant, a sweetener, a spice, a colorant, a flavoring, salts, saccharides, an antioxidant, vitamins, a stabilizer, a thickener, a carrier, an excipient, a lubricant, a surfactant, a propellant, a preservative, a chelating agent, a pH adjuster, and the like. Those other raw materials can be added at any time as long as those do not interfere with the processes described above.

There is no particular limitation on forms of products such as a food or beverage composition, a food or beverage additive, a seasoning, a medicine, and a cosmetic, and can be, for example, a solid (a tablet, powder, granules, or the like), a semi-solid (paste or the like), a liquid (a solution, a suspension, an emulsion, or the like), or an encapsulated product. Types of food and beverage used are not particularly limited, and examples thereof include noodles, processed meat products, processed fish products, processed vegetables, side dishes, confectionery, drinks and the like. Types of the seasoning are also not particularly limited and can be, for example, soup stock, soup, sauce, and the like.

[3. Method for Inhibiting Expression of IL-1β and/or IL-6]

An aspect of the present invention includes, in order to inhibit the expression of IL-1β and/or IL-6, the step of administering, to a subject, an effective amount of the above described expression inhibitor or a composition (e.g., a food or beverage composition, a medicine, or the like) containing the expression inhibitor. The method of administration can be appropriately determined depending on a type of administration subject, an expression inhibitor to be administered, a form of a composition, and the like. In a case where the subject is an individual (human or non-human animal), the administration method is, for example, oral administration. In a case where the subject is a cell, a tissue, or the like, the administration method is, for example, addition into a culture medium.

[4. Method of Preventing and Alleviating Inflammation]

An aspect of the present invention includes, in order to prevent and/or alleviate inflammation, the step of administering, to a human or a non-human animal, an effective amount of the above described expression inhibitor or a composition (e.g., a food or beverage composition, a medicine, or the like) containing the expression inhibitor. The method of administration can be appropriately determined depending on a site at which inflammation that is a subject for prevention and/or alleviation occurs, an expression inhibitor to be administered, a form of a composition, and the like. For example, the administration method is oral administration (oral uptake).

[5. Method of Preventing and Alleviating Fatigue]

An aspect of the present invention includes, in order to prevent and/or alleviate fatigue, the step of administering, to a human or a non-human animal, an effective amount of the above described expression inhibitor or a composition (e.g., a food or beverage composition, a medicine, or the like) containing the expression inhibitor. The method of administration can be appropriately determined depending on a type of fatigue that is a subject for prevention and/or alleviation, an expression inhibitor to be administered, a form of a composition, and the like. For example, the administration method is oral administration (oral uptake).

Aspects of the present invention can also be expressed as follows:

(1) An IL-1β and/or IL-6 expression inhibitor which inhibits expression of IL-1β and/or IL-6, the IL-1β and/or IL-6 expression inhibitor containing a component derived from alcoholic fermentation lees.

(2) The IL-1β and/or IL-6 expression inhibitor described in (1), containing: a water extract of the alcoholic fermentation lees; or a refermented product obtained by fermenting the alcoholic fermentation lees at least once by lactic acid fermentation and/or alcoholic fermentation.

(3) An anti-fatigue composition containing the inhibitor described in (1) and (2) above.

(4) The anti-fatigue composition described in (3), which is for use in prevention of chronic fatigue syndrome.

(5) A food or beverage composition containing: the IL-1β and/or IL-6 expression inhibitor described in (1) or (2) above; or the anti-fatigue composition described in (3) or (4).

(6) The food or beverage composition described in (5), which is a food or beverage for one or more specified health uses, a food or beverage with one or more functional claims, or a food or beverage with one or more nutrient function claims, the food or beverage for one or more specified health uses, the food or beverage with one or more functional claims, and the food or beverage with one or more nutrient function claims each bearing an "anti-fatigue" claim.

(7) A method for alleviating fatigue, the method including the step of: administering, to a human or a non-human animal, at least one selected from the IL-1β and/or IL-6 expression inhibitor described in (1) or (2), the anti-fatigue composition described in (3) or (4), and the food or beverage composition described in (5) or (6).

The present invention is not limited to the embodiments, but can be altered by a skilled person in the art within the scope of the claims. The present invention also encompasses, in its technical scope, any embodiment derived by combining technical means disclosed in differing embodiments.

EXAMPLES

The present invention will be more specifically described below with reference to Examples. Note, however, that the present invention is not limited to those Examples.

Example 1: Manufacture of Sake-Lees Extract (SLE) Powder

Sake lees (i.e., pomace of sake) in an amount of 20 kg and water in an amount of 40 L were stirred with use of a mixer to uniformly dissolve the sake lees. The solution thus obtained was heated to 70° C., and solid-liquid separation was carried out by squeezing to remove a solid content. The solution from which the solid content had been removed was cooled down to 5° C., and filtered through a 2.5-μm filter to obtain a filtrate. After concentrating the filtrate under reduced pressure, heat sterilization was carried out at 90° C., and thus a concentrated liquid was obtained. To the concentrated liquid, 30% by weight of dextrin was added and spray drying was carried out, and thus 2.9 kg of sake-lees extract powder (hereinafter, also referred to as "SLE powder") was obtained.

Example 2: Manufacture of Sake-Lees Fermented Extract (RFSLE) Powder

Sake lees (i.e., pomace of sake) in an amount of 40 kg were mixed with 72 L of water, and lactic acid was added so that pH became 4.5. To this mixture, sake yeast, an amylase agent (in an amount which is 1/2000 of that of sake lees) and a protease agent (in an amount which is 1/800 of that of sake lees) were added, and fermentation was carried out for 3 days at a constant temperature of 25° C. After the fermentation, the solution thus obtained was heated until reaching 70° C. for sterilization, and solid-liquid separation was carried out by squeezing to remove a solid content. Thus, a sake-lees fermented extract was obtained. The sake-lees fermented extract was filtered through a 2.5-μm filter. The filtrate thus obtained was concentrated under reduced pressure and heat sterilization was carried out at 90° C., and thus a concentrated liquid of the sake-lees fermented extract was obtained. To the concentrated liquid of sake-lees fermented extract, 30% by weight of dextrin was added and spray drying was carried out, and thus 3.0 kg of sake-lees fermented extract powder (hereinafter, also referred to as "RFSLE powder") was obtained.

Example 3: Manufacture of Lactic-Acid Fermented RFSLE Powder

The sake-lees fermented extract of Example 2 was adjusted to pH5.5, and the solution was heated to 92.5° C., followed by heat sterilization for 30 minutes. To this solution, a 40-wt % glucose solution was added in an amount of 1/400 with respect to the concentrated liquid of sake-lees fermented extract, and a lactic acid bacterium *Lactobacillus hilgardii* was added by 1% by weight to the concentrated liquid of sake-lees fermented extract whose weight is considered as 100%. The solution was subjected to lactic acid fermentation for 48 hours at 35° C., and then the solution was again heated to 92.5° C. to carry out heat sterilization for 30 minutes. The solution was adjusted to pH5.3 and then centrifuged at a speed of 6500 rpm for 15 minutes to remove a centrifugal supernatant. The solution thus obtained was concentrated under reduced pressure, and 30% by weight of dextrin was added thereto, followed by spray drying to obtain 2.6 kg of lactic-acid fermented RFSLE powder.

Example 4: Verification of Effect of Composition Derived from Sake Lees on Central Nervous System Inflammation Model Rat In a case where polyriboinosinic acid-polyribocytidylic acid (hereinafter referred to as "Poly I:C") which is a synthetic double-stranded RNA is administered to a rat via its abdominal cavity, inflammation occurs in a peripheral tissue, and a signal thereof is conveyed into the brain to induce neuroinflammation in the brain. Transient fever and suppression of spontaneous activity lasting for several days occur (Non-Patent Literature 1). This rat (male SD-line rat: 8 weeks old) was used as a central nervous system inflammation model rat to verify an effect of the composition derived from sake lees. Note that this central nervous system inflammation model rat is used as a fatigue model animal.

The compositions derived from sake lees of Examples 1 through 3 were used, and each of those compositions was uniformly mixed with a regular diet (MF available from Oriental Yeast Co., Ltd.) at a weight ratio of 1:1, and then a small amount of water was added to form the mixture into a columnar shape. The mixture thus shaped was freeze-dried, and was used as a feed for animal testing. After ad libitum feeding of the test feed to model rats for 7 days, Poly I:C was administered to the rats and, 5 hours later, samples of a cerebral cortex and a hippocampus were obtained from each rat. An implementation schedule is shown in FIG. 1.

As comparative examples, two types were used: rats ((1) Vehicle+regular diet group) receiving normal diet and a physiological saline solution instead of Poly I:C; and rats ((2) Poly I:C+regular diet group) receiving normal diet and Poly I:C.

As an assessment of central nervous system inflammation, mRNA expression of IL-1β, IL-6, and TNF-α, which are typical inflammatory cytokines serving as markers of inflammation was checked using a semiquantitative RT-PCR method (qRT-PCR method).

[Results]

The results of the verification are shown in FIG. 2. As shown in FIG. 2, the expression of cytokines was significantly enhanced in the cerebral cortex and hippocampus in (2) Poly I:C+regular diet group, while the expression of IL-1beta, IL-6 by Poly I:C administration was significantly inhibited in the three groups ((3), (4), and (5)) in which the test feeds were given. In contrast, the test feeds were not very effective with respect to enhancement of the expression of TNF-α. As such, it is thus clarified that the composition derived from sake lees exhibits an anti-inflammatory effect and an anti-fatigue effect.

INDUSTRIAL APPLICABILITY

The present invention can provide the IL-1β and/or IL-6 expression inhibitor. The IL-1β and/or IL-6 expression inhibitor in accordance with an aspect of the present invention brings about the anti-fatigue effect, and the IL-1β and/or IL-6 expression inhibitor can be used in prevention of chronic fatigue syndrome.

What is claimed is:

1. A method for alleviating fatigue caused by brain inflammation, said method comprising the step of:
    administering, to a human or a non-human animal, an anti-fatigue composition comprising a component derived from alcoholic fermentation lees,
    wherein the component derived from alcoholic fermentation lees is a water extract of the alcoholic fermentation lees or a re-fermented product obtained by fermenting the alcoholic fermentation lees at least once by lactic acid fermentation and/or alcoholic fermentation.

2. A method for alleviating fatigue caused by brain inflammation, said method comprising the step of:
    administering, to a human or a non-human animal, a food or beverage composition comprising a component derived from alcoholic fermentation lees,
    wherein the component derived from alcoholic fermentation lees is a water extract of the alcoholic fermentation lees or a re-fermented product obtained by fermenting the alcoholic fermentation lees at least once by lactic acid fermentation and/or alcoholic fermentation.

3. The method according to claim 1, wherein the brain inflammation is caused by expression of IL-1β and/or IL-6.

4. The method according to claim 3, wherein the component derived from alcoholic fermentation lees inhibits expression of IL-1β and/or IL-6.

5. The method according to claim 1, wherein the alcoholic fermentation lees are sake lees.

6. The method according to claim 3, wherein the alcoholic fermentation lees are sake lees.

7. The method according to claim 4, wherein the alcoholic fermentation lees are sake lees.

8. The method according to claim 2, wherein the brain inflammation is caused by expression of IL-1β and/or IL-6.

9. The method according to claim 8, wherein the component derived from alcoholic fermentation lees inhibits expression of IL-1β and/or IL-6.

10. The method according to claim 2, wherein the alcoholic fermentation lees are sake lees.

11. The method according to claim 8, wherein the alcoholic fermentation lees are sake lees.

12. The method according to claim 9, wherein the alcoholic fermentation lees are sake lees.

* * * * *